(12) United States Patent
Viswanathan

(10) Patent No.: US 7,505,615 B2
(45) Date of Patent: Mar. 17, 2009

(54) PREOPERATIVE AND INTRA-OPERATIVE IMAGING-BASED PROCEDURE WORKFLOW WITH COMPLEXITY SCORING

(75) Inventor: Raju R. Viswanathan, St. Louis, MO (US)

(73) Assignee: Stereotaxis, Inc., St. Louis, MO (US)

( * ) Notice: Subject to any disclaimer, the term of this patent is extended or adjusted under 35 U.S.C. 154(b) by 382 days.

(21) Appl. No.: 11/429,669

(22) Filed: May 5, 2006

(65) Prior Publication Data

US 2006/0270927 A1    Nov. 30, 2006

Related U.S. Application Data

(60) Provisional application No. 60/678,323, filed on May 6, 2005.

(51) Int. Cl.
*G06K 9/00* (2006.01)
*A61B 5/05* (2006.01)

(52) U.S. Cl. .................................. 382/128; 600/407
(58) Field of Classification Search ............ 382/128, 382/129, 130, 131, 132, 133, 134; 378/4, 378/21, 22, 23, 24, 25, 26, 27; 600/407, 600/410, 411, 425, 427, 442, 471, 581, 595; 601/2, 3; 604/99.04, 102.02, 507, 526, 527, 604/532

See application file for complete search history.

(56) References Cited

U.S. PATENT DOCUMENTS

| 5,840,026 A * | 11/1998 | Uber et al. ............... 600/431 |
| 6,241,671 B1 * | 6/2001 | Ritter et al. ............. 600/427 |
| 6,436,058 B1 * | 8/2002 | Krahner et al. .......... 600/587 |
| 6,875,176 B2 | 4/2005 | Mourad et al. |
| 6,901,277 B2 * | 5/2005 | Kaufman et al. ......... 600/407 |
| 2005/0075544 A1 * | 4/2005 | Shapiro et al. .......... 600/300 |

OTHER PUBLICATIONS

International Search Report and Written Opinion Dated: Jul. 15, 2008 pp. 12.

* cited by examiner

*Primary Examiner*—Abolfazl Tabatabai
(74) *Attorney, Agent, or Firm*—Harness, Dickey & Pierce, P.L.C.

(57) ABSTRACT

A method of screening subjects for medical procedures involving the remote navigation of a medical device through the vasculature in an operating region. The method includes processing the image data of the operating region to determine a measure of the complexity of at least a portion of the vasculature in the operating region; and generating a recommendation about at least one parameter of the procedure based at least in part upon a comparison between the determined measure of complexity and a predetermined value.

48 Claims, 1 Drawing Sheet

PREOPERATIVE AND INTRA-OPERATIVE IMAGING-BASED PROCEDURE WORKFLOW WITH COMPLEXITY SCORING

CROSS-REFERENCE TO RELATED APPLICATIONS

This application claims the benefit of U.S. Provisional Patent Application Ser. No. 60/678,323, filed May 6, 2005, the entire disclosure of which is incorporated herein.

FIELD OF THE INVENTION

This invention relates to medical procedures involving the navigations of medical devices through body lumens, such as blood vessels, and in particular to characterizing the body lumen prior to the procedure to facilitate the procedure.

BACKGROUND OF THE INVENTION

A wide variety of non-invasive or minimally invasive medical procedures are conducted by navigating a medical device through a body lumen (typically the vasculature) to the procedure sight. A primary limitation on these types of procedures is the ability to navigate through the lumen, which is determined by a number of factors, including the character (e.g. the size and tortuoisity of the lumen). Various remote and automated remote navigation systems have been developed to assist or facilitate navigation through body lumens, one example of such a system is a magnetic navigation system that remotely orients the distal end to a medical device such as the Telstar system or the Niobe system available from Stereotaxis. However, even with the assistance of a remote navigations system or an automate remote navigation system, the size and tortuoisity of the body lumens is still an important factor in conducting the procedure.

Presently the size and tortuoisity is not taken into account in any systematic and orderly and consistent manner. The physician may or may not have images available from which to make an opinion or judgment about the vasculature and often has not basis on which to make decisions about who should perform the procedure, where it should be performed, what equipment should be used, how the procedure should be conducted, and the path that should be taken.

SUMMARY OF THE INVENTION

Generally, in accordance with the preferred embodiment of the present invention, medical image data of the procedure sight is processed to reach some value representative of the complexity of the body. The imaging data may be data from any medical imaging system from which the path of the lumen can be evaluated, including x-ray, MRI, ultrasound, etc. The value representative of the complexity of the body lumen may be some indication of one or more of the minimum lumen dimension, the number of bends exceeding a predetermined thresholds. The minimum distance between bends of exceeding predetermined thresholds or any other indicator relevant to any parameter of conducting a procedure involving navigation through the vasculature.

In various preferred embodiments of this method the determined value representative of the complexity of the body lumen, can be used to recommend or to determine some parameter of the procedure. For example based upon value representative of the complexity of the body lumen, a recommendation can be made (or it can be determined) who should conduct the procedure, where (what facility should be used) the procedure should be conducted, how the procedure should be conducted, when the procedure should be conducted, with what equipment the procedures should be conducted.

Alternatively, the value representative of complexity of the body lumen can be used to predict the duration of the procedure. This prediction can be based solely on the value representative of the complexity of the body lumen, or it can be also taken into consideration other parameters of the procedures such as who will conduct the procedure, where the procedure will be conducted, how the procedure will be conducted, or what equipment will be used. The predicted duration can then be used to recommend or to determine other parameters of the procedure.

The value representative of the complexity of the lumen and/or a predicted duration based in whole or I part thereon, can be used to make a recommendation or a determination between the alternative paths.

DETAILED DESCRIPTION OF THE PREFERRED EMBODIMENTS

Figure 1:
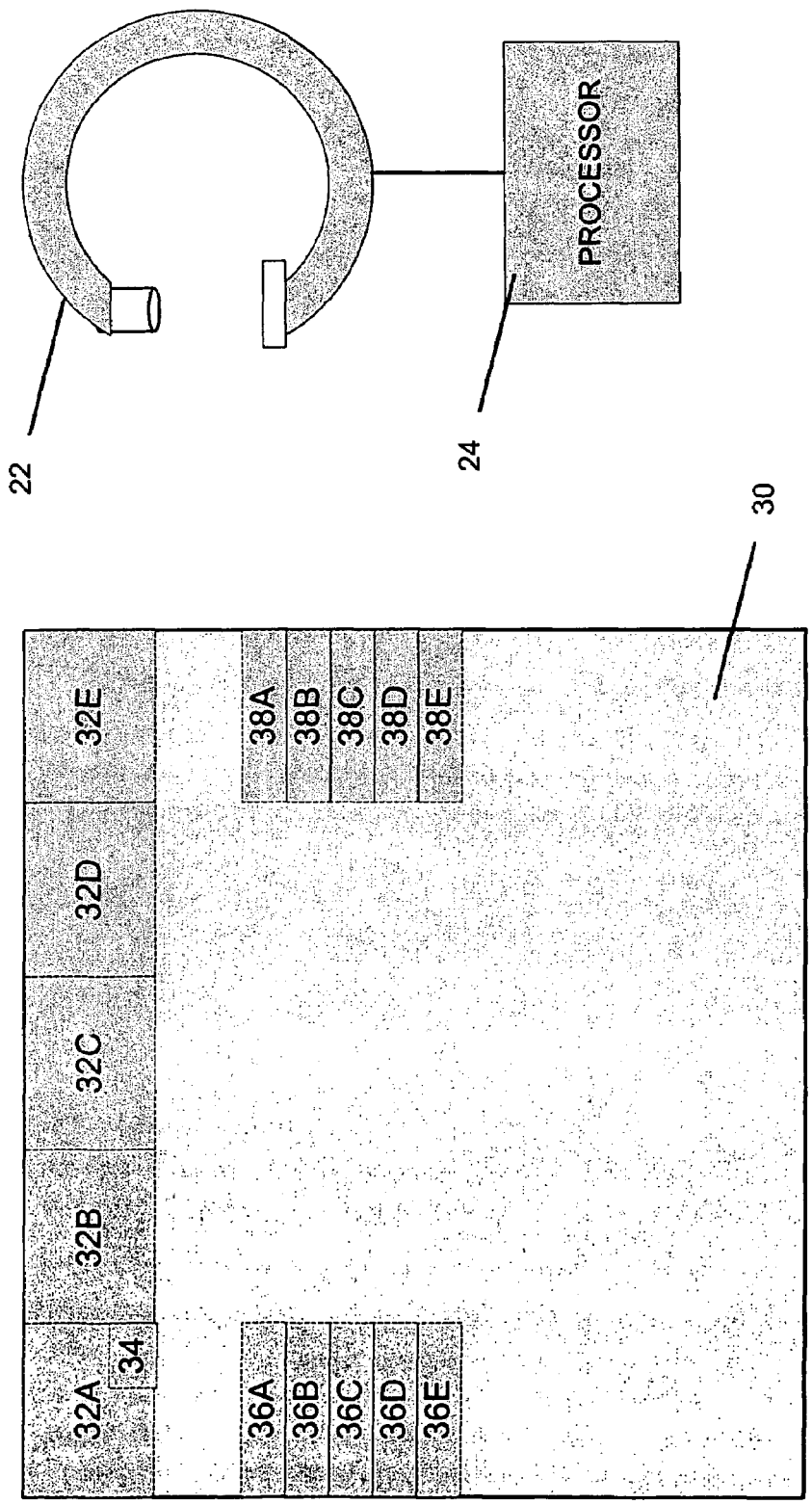
FIG. 1 is a schematic diagram of one possible implementation of a system and method in accordance with the principles of this invention.

One possible implementation of a system 20 and method in accordance with the principles of this invention is illustrated schematically in FIG. 1. The system 20 can include imaging apparatus 22 for imaging the procedure site in the subject, and a processor 24 for processing image data and determining some value representative of the complexity of the body lumen.

The imaging apparatus 22 can be an x-ray imaging apparatus, an MRI imaging apparatus, an ultrasound imaging apparatus or any other imaging system that can provide processable image data from which a value representative of the complexity of the body lumen can be determined.

The processor can be any processor for processing image data. The processor can be programmed or otherwise adapted to process image data from the procedure site from the imaging system 22.

While as illustrated the imaging apparatus and the processor are adjacent, that is not necessary and the imaging apparatus 22 could be remote from the processor 24. Moreover, the processing can take place contemporaneously with or the processing can take hours, days, or even longer after the imaging.

The system 20 is adapted for use in an integrated medical facility such as a cardiac catheter laboratory 30 (cardiac cath lab). The cardiac cath lab 30 is shown schematically in FIG. 1 as comprising a plurality of treatment rooms 32A, 32B, 32C, 32D and 32E. The various treatment rooms may have different equipment for accommodating a variety of procedures. For example, treatment rooms 32A may be provided with a remote navigation system 34, such as a remote magnetic navigation system.

A variety of different devices, such as catheters 36A, 36B, 36C, 36D and 36F, are inventoried and available each with different physical properties (for example, stiffness, bending radius, etc.) making them suited for different navigations. In some embodiments the system 20 keeps track of the inventory and can even automatically reorder devices as they are used. In embodiments where the system 20 either recommends or specifies the devices to be used in the procedure, the system can do so taking into account the devices that are available at the facility 30.

Typically, several different physicians (represented as 38A, 38B, 38C, 38D and 38E) are available for performing procedures in the facility 30.

In one embodiment of a method in accordance with the principles of this invention, the procedure site in a subject is imaged using the imaging system 22. This imaging would typically be conducted at the facility 30 just prior to the procedure, but could also be done at some earlier time. Existing image data from the subject's medical records could also be used.

The imaging data of the procedure site is processed by processor 24 to determine one or more values representative of the navigable body lumens in the procedure site. These one or more values could be single composite of a number of separate measures, a single value representative of a single measure, or a plurality of values representative of a plurality of measures. These measures can include one or more of the following: measure of greatest bend; the number of bends that exceed a predetermined threshold; the number of bends that exceed each of a plurality of predetermined thresholds, the minimum distance between bends that exceed a predetermined threshold; the rotation angle between the planes of adjacent bends; the minimum size of the lumen, or any other measures of the tortuosity of the lumen that can is useful in determining either the difficulty of the navigation, the ability or in ability of certain medical devices to pass through the lumens, the time it would take to navigate through the lumen, and/or the ability of a particular physician to navigate through the lumen.

Complexity Scoring Details

There are several measures of procedural complexity that would be useful to evaluate lumen construction. While this description will focus on the subject's vasculature as the principal pathway for navigation, it is not so limited, and the system can be used for navigation through other lumens or passages in the body as well. In addition to the measures described below, other measures can be evaluated in pre-clinical studies to assess their impact on overall procedure complexity. These measures can be processed into a single recommendation or indication relating to the procedure, for example when to conduct the procedure manually and when to conduct the procedure with an automated navigation system, such as with an automated magnetic navigation system. The particular measure can be based solely on the vasculature itself, or it can depend upon both the vasculature and the type of procedure being conducted, and/or the particular pathway selected for the procedure being conducted.

In the case of a vessel tree (i.e., including bifurcations/branches), the indices in (1) and (2) below are computed for the path from the initial (most proximal) point to the lesion endpoint.

(1) Angle Changes:

The vessel is reconstructed from the imaging data, and a set of local curvature maximums is determined from the reconstructed centerline of the vessels. For each such point $p_i$ that is a local curvature maximum, the magnitude of the curvature is integrated over a predetermined length, e.g. 30 mm centered at point $p_i$. The result yields an angular measure $t_i$ (converted from radians to degrees). The number of local curvature maxima n exceeding a predetermined level, e.g. $t_i>70$ degrees be n. If along the path there is at least one pair of successive local curvature maxima $p_i$ and $p_{i+1}$ separated by a length less than a predetermined distance (e.g. 4 cm, and if $(t_i+t_{i+1})>70$ degrees, define m=1 (otherwise, m=0).

One complexity index, an integer M, can be defined as M=max (m, n).

(2) Lesion

The reconstruction software is preferably capable of identifying at least one lesion. For an identified lesion, $d_{max}$ and $d_{min}$ are the maximum and minimum vessel diameter along the lesion and r is the ratio ($d_{min}/d_{max}$). If there is at least one local curvature maximum $p_i$ along the lesion with $t_i>40$ degrees, and in addition if r<0.6, a measure N is set to: N=1 (otherwise N=0).

(3) Branch Properties:

Along a path going from the proximal point on the vessel tree to the lesion, it may go through a series of branches or bifurcations. At each bifurcation, $\beta$ is the branch angle and $d_1$ and $d_2$ are the parent and daughter branch diameters (in centimeters) respectively. Where the parent is the vessel just proximal to the bifurcation and the daughter branch (just distal to the bifurcation) is defined as the branch heading towards a lesion, a measure A is set to: $A=(1-\cos\beta)/d_2$, and P=0. If $A>\pi/4$, then P=1. Otherwise, find $\beta_1$ such that $(1-\cos(\beta-\beta_1))/(1-\cos\beta)=(d_2/d_1)$. Define $B=(1-\cos\beta_1)/d_1$. If $B>\pi/4$, define P=1. In principle, this is repeated for every relevant branch on the path until the end of the lesion or until P=1, whichever comes first.

The indices (M, N, P) are the desired complexity indices. Initially we would want to use all three; later it is possible that even a single non-zero value in this set may indicate a case for Magnetic Navigation.

Selecting the Manner of Conducting a Procedure

In accordance with one preferred embodiment, a method is provided for facilitating the selection of the manner of conducting a medical procedure. Remote navigation systems, such as remote magnetic navigation systems, can facilitated difficult navigations (for example, navigations through sharp turns, or navigation through excessive turns, etc.) over manual navigations. However, for some navigations (for example, a substantial straight navigation) a manual navigation may be just as fast or even faster than navigation using a remote navigation system. Since manual navigation doesn't tie up an expensive remote navigation system, it is preferable to use manual navigation where the procedure can be performed in similar time frame, with roughly success rate, and similar patient affect.

The vasculature through which the procedure will be performed can be scored as provided herein, and this score can be used as an aid in selecting the type of procedure (e.g., manual navigation vs. automated or semi-automated navigation). In accordance with one aspect of this invention, the score can be compared with a threshold number and depending upon this comparison a recommendation made to perform the procedure manually or to use a remote navigation system to assist with or to conduct the navigation. The comparison can be done manually, for example on a look up table, but can also be done automatically by computer. Because the skill levels of physicians vary, threshold values can be established for each physician thus, a different recommendation might be reached for the same complexity score, depending upon the thresholds of the available physicians. These thresholds can be determined by experience level (e.g., length or experience or number of procedures). These thresholds can also be determined by the actual experience of the physicians in cases with similar complexity scores. A computer can track each physician's performance (e.g., success rate, procedure duration, or other parameter) and automatically determine a threshold.

In accordance with another aspect of the invention the complexity score can include multiple values and the threshold can comprise multiple values and the comparison can involve comparing the various values comprising the complexity score and the threshold. Some of the comparisons of these values can be weighted.

EXAMPLE 1A

The operating region of a subject is imaged, the image data is processed and a single value complexity score is determined. For example, a score of 89 is determined for the vasculature. A threshold is established for the facility of 85. Since the score is above the threshold, the system might recommend that the procedure be performed with the assistance of a remote navigation system.

EXAMPLE 1B

The operating region of a subject is imaged, the image data is processed and a single value complexity score is determined. For example, a score of 89 is determined. The physicians available at the facility have threshold scores of: Physician 1 (82); Physician 2 (88); Physician 3 (90); Physician 4 (92); and Physician 5 (95). If physicians 1 and 2 are scheduled for the procedure, the system might recommend that these physicians use a remote navigation system, since their thresholds are below the complexity score for the procedure. However, if physicians 3, 4, or 5 are scheduled for the procedure, the system might recommend that these physicians conduct the procedure manually since their thresholds are above the complexity score for the procedure.

EXAMPLE 1C

The operating region of a subject is imaged, the image data is processed and a multiple value complexity score is determined. For example, a complexity score of 89.91.85 is determined, each value representing a particular aspect of the complexity of the vasculature. The physicians available at the facility have threshold scores of: Physician 1 (82.90.85); Physician 2 (88.92.87); Physician 3 (90.95.84); Physician 4 (92.92.92); and Physician 5 (95.96.90). If physicians 1, 2, or 3 are scheduled for the procedure, the system might recommend that these physicians use a remote navigation system, since their thresholds for at least one of the values are below at least one of the values for the complexity score for the procedure. However, if physicians 4 or 5 are scheduled for the procedure, the system might recommend that these physicians conduct the procedure manually since their thresholds for all of the values are above the complexity score for the procedure.

Selecting the Devices Used for Conducting a Procedure

In accordance with one preferred embodiment, a method is provided for facilitating the selection of the medical devices used for conducting a medical procedure. Various device are typically available for conducting a particular procedure typically with different diameters, stiffness or flexibility, and different stiffness/flexibility profiles. However in addition to these physical characteristics, there are usually competing performance and functional considerations, so it is not always a matter of simply choosing the smallest and most flexible device possible.

The vasculature through which the procedure will be performed can be scored as provided herein, and this score can be used as an aid in selecting the type of device, either by corresponding physical properties or by selecting a specific device. In accordance with one aspect of this invention, the complexity score can be used to determine certain threshold properties such as maximum dimension, maximum stiffness, minimum flexibility, minimum bending diameter, etc. In accordance with another aspect of this invention, the complexity score can be compared with a threshold number for each of a plurality of devices and depending upon this comparison a recommendation made as to which device to use. The comparison can be done manually, for example on a look up table, but can also be done automatically by computer.

Because the skill levels of physicians vary, threshold values can be established for each physician thus, a different recommendation might be reached for the same complexity score, depending upon the thresholds of the available physicians. These thresholds can be determined by experience level (e.g., length or experience or number of procedures). These thresholds can also be determined by the actual experience of the physicians in cases with similar complexity scores. A computer can track each physician's performance (e.g., success rate, procedure duration, or other parameter) and automatically determine a threshold.

In accordance with another aspect of the invention the complexity score can include multiple values and the threshold for the devices can comprise multiple values and the comparison can involve comparing the various values comprising the complexity score and the threshold. Some of the comparisons of these values can be weighted.

EXAMPLE 2A

The operating region of a subject is imaged, the image data is processed and a single value complexity score is determined. For example, a score of 89 is determined for the vasculature. Five different devices are available with thresholds of: Device 1 (85); Device 2 (87); Device 3 (89); Device 4 (92); and Device 5 (99). Because the thresholds of the Devices 1 and 2 are below the complexity score for the procedure, they would not be recommended. Because the thresholds of the Devices 3, 4, and 5 are equal to or above the complexity score, each could be used in the procedure. Depending upon how the complexity score is determined, how the threshold is determined, and the performance properties of the devices, the selection among Devices 3, 4, and 5 may be at the physician's election. Alternatively, the performance properties of the device may have an inverse relation to the threshold value, in which case the device with the lowest acceptable threshold value (Device 3) would be selected.

EXAMPLE 2B

The operating region of a subject is imaged, the image data is processed and a single value complexity score is determined. For example, a score of 89 is determined for the vasculature. Five different devices are available with thresholds of: Device 1 (85); Device 2 (87); Device 3 (89); Device 4 (92); and Device 5 (99). Five different physicians are also available to perform the procedure, each with a different experience threshold: Physician 1 (85); Physician 2 (88); Physician 3 (90); Physician 4 (95) and Physician 5 (99). Because the thresholds of the Devices 1 and 2 are below the complexity score for the procedure, they would not be recommended. Because the thresholds of the Devices 3, 4, and 5 are equal to or above the complexity score, each could be used in the procedure. Depending upon how the complexity score is determined, how the threshold is determined, and the performance properties of the devices, the selection among Devices 3, 4, and 5 may be at the physician's election. Alternatively, the performance properties of the device may have an inverse relation to the threshold value, in which case the device with the lowest acceptable threshold value (Device 3) would be selected. The selection among Devices 3, 4, and 5 may also be based upon the Physician performing the procedure. For example, if Physicians 1 or 2 were performing the procedure, Device 5 might be recommended, since their thresholds are below the complexity score for the procedure, and the enhanced maneuverability may be valuable. If Physician 3 were performing the procedure Devices 4 or 5 might be recommend, since this physician's threshold is just barely above the complexity score for the procedure. If Physician 4 were performing the procedure, Devices 3 or 4 might be recommended since this physician's threshold is well above the complexity score. Lastly, if Physician 5 were performing the procedure, Device 3 might be recommended since this physician's threshold is well above the complexity score for the procedure.

EXAMPLE 2C

The operating region of a subject is imaged, the image data is processed and a multiple value complexity score is determined. For example, a complexity score of 89.91.85 is determined, each value representing a particular aspect of the complexity of the vasculature. There are five devices available for the procedure. The devices have threshold scores of: Device 1 (82.90.85); Device 2 (88.92.87); Device 3 (90.95.84); Device 4 (92.92.92); and Device 5 (95.96.90). Devices 1, 2, or 3 would not be recommended for the procedure since their thresholds for at least one of the values are below at least one of the values for the complexity score for the procedure. However, either Device 4 or Device 5 might be recommended for the procedure because their thresholds for all of the values are above the complexity score for the procedure. The selection between Device 4 and Device 5 might be made to select the device with the minimum thresholds that exceed the complexity score, or be left to the physician, or the selection might be based upon the physician conducting the procedure. If none of the devices had thresholds exceeding the values of the all of the complexity scores, a selection could be made based on the device that was below the complexity score by the least amount. The various values in the complexity score and the thresholds can be weighted and the comparison made based upon these weights.

Selecting the Physician to Perform a Procedure

In accordance with one preferred embodiment, a method is provided for facilitating the selection of a physician for performing a medical procedure. Physicians can have a wide range of experience and physical dexterity. Some navigations are very straight forward, while others may require a high degree of experience and/or physical dexterity. Often times a procedure can be conducted by physicians of any experience and skill level, but a physician with more experience and/or more skill could perform the procedure faster or with less risk than physicians of less experience and/or less skill.

The vasculature through which the procedure will be performed can be scored as provided herein, and this score can be used as an aid in selecting the physician for performing the procedure. In accordance with one aspect of this invention, the score can be compared with a threshold number and depending upon this comparison a recommendation made as to who should perform the procedure. The comparison can be done manually, for example on a look up table, but can also be done automatically by computer. Because the skill levels of physicians vary, threshold values can be established for each physician. These thresholds can be determined by experience level (e.g., length or experience or number of procedures). These thresholds can also be determined by the actual experience of the physicians in cases with similar complexity scores. A computer can track each physician's performance (e.g., success rate, procedure duration, or other parameter) and automatically determine a threshold.

In accordance with another aspect of the invention the complexity score can include multiple values and the threshold can comprise multiple values and the comparison can involve comparing the various values comprising the complexity score and the threshold. Some of the comparisons of these values can be weighted.

EXAMPLE 3A

The operating region of a subject is imaged, the image data is processed and a single value complexity score is determined. For example, a score of 89 is determined for the vasculature. The physicians available at the facility have threshold scores of: Physician 1 (82); Physician 2 (88); Physician 3 (90); Physician 4 (92); and Physician 5 (95). The system would not recommend that Physicians 1 or 2 be scheduled to perform the procedure because their thresholds are below the complexity score for the procedure. The system would recommend that Physicians 3, 4, or 5 be scheduled for the procedure. The selection among Physicians 3 and 4 and 5 can be based upon availability, work load, or other factors. The selection of the physician might also be affected by the selection of devices, the selection of how the procedure will be performed, etc.

EXAMPLE 3B

The operating region of a subject is imaged, the image data is processed and a multiple value complexity score is determined. For example, a complexity score of 89.91.85 is determined, each value representing a particular aspect of the complexity of the vasculature. The physicians available at the facility have threshold scores of: Physician 1 (82.90.85); Physician 2 (88.92.87); Physician 3 (90.95.84); Physician 4 (92.92.92); and Physician 5 (95.96.90). The system might not recommend that Physicians 1, 2, or 3 be scheduled for the procedure because their thresholds for at least one of the values are below at least one of the values for the complexity score for the procedure. The system would recommend Physicians 4 or 5 are scheduled for the procedure because their thresholds for all of the values are above the complexity score for the procedure. The selection between Physicians 4 and 5 may be based upon the physician whose threshold exceeds the complexity score by the greatest margin, or upon other factors. In making the selection, the various values comprising the complexity scores can be weighted.

If no available physician has a threshold that exceeds the complexity score, than the physician closest to the complexity score can be recommended. In making this determination using multiple value complexity scores, the various values can be weighted.

Selecting the Path for Conducting a Procedure

In accordance with one preferred embodiment, a method is provided for facilitating the selection among one of several paths through a vasculature network. For some medical procedures, there may be two or more paths through the subject's vasculature to reach the site for conducting the procedure. However, the paths are typically not equivalent from a navigation standpoint. It would be desirable to be able to select that path that provides the easiest navigation, or the fastest navigation, or the least risky navigation.

The alternative paths through the vasculature through which the procedure will be performed can be scored as provided herein, and this score can be used as an aid in selecting the type of procedure (e.g., manual navigation vs. automated or semi-automated navigation). In accordance with one aspect of this invention, the scores can be compared directly to determine the path with the lowest complexity score. The comparison can be done manually, but can also be done automatically by computer. The comparison can take into accound other factors, including the availability of the assistance of a remote navigation system, the experience and skill levels of the physicians available, and the types of devices available to perform the procedure, These additional factors may favor a path with a high complexity score.

In accordance with another aspect of the invention the complexity score can include multiple values and these multiple-value complexity scores for each path can be compared by comparing these individual values. Some of the comparisons of these values can be weighted.

EXAMPLE 4A

The operating region of a subject is imaged, the image data is processed and a single value complexity score is determined for each of at least two paths. For example, a score of 89 is determined for Path 1 and a score of 92 is determined for Path 2. Since the complexity score of Path 1 is lower than the complexity score for Path 2, the system would typically recommend Path 1. However other factors such as the availability of an automated navigation system, the experience and skill of the available physicians, and the types of devices available may change the recommendation, particularly where the complexity scores for the paths are close.

EXAMPLE 4B

The operating region of a subject is imaged, the image data is processed and a multiple value complexity score is determined for each of at least two paths. For example, a complexity score of 89.91.85 is determined for Path 1 and a complexity score of 90.91.90 is determined for Path 2. The scores are compared, and the system would typically recommend Path 1, because the value for each component of the complexity score is lower than the corresponding component of the complexity score for Path 2. However other factors such as the availability of an automated navigation system, the experience and skill of the available physicians, and the types of devices available may change the recommendation, particularly where the complexity scores for the paths are close. Moreover, the individual values for each of the complexity scores can be weighted, particular where no Path has the lowest value for each of the values.

Estimating the Duration of a Procedure

In accordance with one preferred embodiment, a method is provided for estimating the duration of a medical procedure. The duration of many procedures depends significantly on the complexity of the vasculature through which the medical devices must be navigated. An estimate of the duration of many procedures can be made based upon the complexity of the vasculature.

The vasculature through which the procedure will be performed can be scored as provided herein, and this score can be used as an aid in selecting the type of procedure (e.g., manual navigation vs. automated or semi-automated navigation). In accordance with one aspect of this invention, the score can be compared with a table of time versus complexity score for the particular type of procedure. The comparison can be done manually, for example on a look up table, but can also be done automatically by computer. Alternatively, a formula or equation can be developed to estimate the duration of a particular type of procedure based the complexity score for the vasculature. Data for procedures can be processed to develop and update the lookup table or formula.

Because there are other variables that can effect the duration of the procedure, these can be taken into account in formulating the lookup table or equation. For example, the look up table or the formulation can be specific to the method of conducting the procedure (with or without the assistance of an automated navigation system), the physician conducting the procedure, the devices used, etc.

In accordance with another aspect of the invention the complexity score can include multiple values and these multiple values can be used to more accurately estimate the duration of the procedure.

EXAMPLE 5A

The operating region of a subject is imaged, the image data is processed and a single value complexity score is determined. For example, a score of 89 is determined for the vasculature. This complexity score is used to determine an estimated duration in a look-up table for the specific procedure. Look-up tables may be provided for specific methods, specific physicians, and specific devices. Alternatively, the complexity score can be used as a variable in a function for estimating the duration of the procedure. Other variables can include values for the method of conducting the procedure, the physician conducting the procedure, and the devices used, etc.

EXAMPLE 5B

The operating region of a subject is imaged, the image data is processed and a multiple value complexity score is determined. For example, a complexity score of 89.91.85 is determined. This complexity score is used to determine an estimated duration in a look-up table for the specific procedure. Look-up tables may be provided for specific methods, specific physicians, and specific devices. Alternatively, the complexity score can be used as variables in a function for estimating the duration of the procedure. Other variables can include values for the method of conducting the procedure, the physician conducting the procedure, and the devices used, etc.

Scheduling a Procedure

In accordance with one preferred embodiment, a method is provided for scheduling medical procedures. Procedures in medical facilities with multiple procedure rooms and multiple physicians must be scheduled efficiently, in order to minimize unused procedure room and avoid wasting physician time. However, the length and complexity of medical procedures varies from patient to patient, even when the exact same procedure is being performed.

The vasculature through which the procedure will be performed can be scored as provided herein, and this score can be used as an aid in estimating the difficulty of the procedure and the duration of the procedure, so that the procedure can be efficiently scheduled. This scheduling can include assigning both a time in a procedure room and/or a physician to perform the procedure. In accordance with one aspect of this invention, the complexity score is used to determine the duration of the procedure, so that the procedure can be assigned to a procedure room with available time. The estimated duration can be determined using a look-up table or a formula. The look-up table or formula can take into account other aspects such as the type of procedure, the method for conducting the procedure (e.g. with or without the assistance of an automated navigation system), the experience and skill of the physician conducting the procedure, and the devices selected to perform the procedure.

The scheduling can be done manually based upon the complexity score, but can also be done automatically by computer. The scheduling may take into account a physician assigned to the case, or assigning a physician may be part of the scheduling. Similarly, the scheduling may take into account the decision to use or not to use an automated navigation system, or this selection can be part of the scheduling. Lastly the scheduling may take into account the devices selected for conducting the procedure, or this selection can be part of the scheduling.

In accordance with another aspect of the invention the complexity score can include multiple values and these values can be used to determine an estimated duration for the procedure, and may also be used to help select how the procedure will be performed, who will perform the procedure, what devices will be used to perform the procedure.

EXAMPLE 6A

The operating region of a subject is imaged, the image data is processed and a single value complexity score is determined. For example, a score of 89 is determined for the vasculature. Based upon this complexity score, an estimate can be made of the duration of the procedure. This estimate may or may not take into account factors such as the type of procedure, how the procedure will be conducted, who will conduct the procedures, and what devices will be used to conduct the procedure. With an estimated duration for the procedure, the system can recommend one or more procedure rooms and one or more start times based on the procedures that have already been scheduled. If the estimate takes into account how the procedure will be conducted, then the system will limit recommendation to rooms where the procedure can be performed in the selected manner (e.g., if the procedure is to be performed with the assistance of a remote navigation system, the system will limit the recommendation to a room with the require remote navigation system. Similarly, if the estimate takes into account the physician who will conduct the procedure, then the system will limit the recommended times to times that that physician is not already scheduled to conduct a procedure.

The system can also use the complexity score to make several recommendations of room, method of conducting the procedure, physician to conduct the procedure, and devices to use to conduct the procedure, and start time. One of the various recommendations can be selected, or the system can automatically select the best recommendation, and present the lesser recommendations as optional overrides.

EXAMPLE 6B

The operating region of a subject is imaged, the image data is processed and a multiple value complexity score is determined. For example, a complexity score of 89.91.85 is determined, each value representing a particular aspect of the complexity of the vasculature. Based upon this complexity score, an estimate can be made of the duration of the procedure. This estimate may or may not take into account factors such as the type of procedure, how the procedure will be conducted, who will conduct the procedures, and what devices will be used to conduct the procedure. With an estimated duration for the procedure, the system can recommend one or more procedure rooms and one or more start times based on the procedures that have already been scheduled. If the estimate takes into account how the procedure will be conducted, then the system will limit recommendation to rooms where the procedure can be performed in the selected manner (e.g., if the procedure is to be performed with the assistance of a remote navigation system, the system will limit the recommendation to a room with the require remote navigation system. Similarly, if the estimate takes into account the physician who will conduct the procedure, then the system will limit the recommended times to times that that physician is not already scheduled to conduct a procedure.

The system can also use the complexity score to make several recommendations of room, method of conducting the procedure, physician to conduct the procedure, and devices to use to conduct the procedure, and start time. One of the various recommendations can be selected, or the system can automatically select the best recommendation, and present the lesser recommendations as optional overrides.

Based upon this complexity score, an estimate can be made of the duration of the procedure. This estimate may or may not take into account factors such as the type of procedure, how the procedure will be conducted, who will conduct the procedures, and what devices will be used to conduct the procedure. With an estimated duration for the procedure, the system can recommend one or more procedure rooms and one or more start times based on the procedures that have already been scheduled. If the estimate takes into account how the procedure will be conducted, then the system will limit recommendation to rooms where the procedure can be performed in the selected manner (e.g., if the procedure is to be performed with the assistance of a remote navigation system, the system will limit the recommendation to a room with the require remote navigation system. Similarly, if the estimate takes into account the physician who will conduct the procedure, then the system will limit the recommended times to times that that physician is not already scheduled to conduct a procedure.

The system can also use the complexity score to make several recommendations of room, method of conducting the procedure, physician to conduct the procedure, and devices to use to conduct the procedure, and start time. One of the various recommendations can be selected, or the system can automatically select the best recommendation, and present the lesser recommendations as optional overrides.

The various values comprising the complexity score can be used in different aspects of the scheduling. For example some of the values may be weighted more heavily in estimating the procedure duration, some of the values may be weighted more heavily in determining how to conduct the procedure, some of the values may be weighted more heavily in determining the physician to perform the procedure, and some of the values can be more heavily weighted in determining what devices to use to perform the procedure.

These and other procedure parameters can be recommended or determined based upon either a single value or multiple value complexity score of the vasculature.

Operation

In one of its preferred embodiments, the invention provides a method of screening subjects for medical procedures involving the remote navigation of a medical device through the vasculature in an operating region. The method comprises processing image data of the operating region to determine a measure of the complexity of at least a portion of the vasculature in the operating region, and generating a recommendation about at least one parameter of the procedure based at least in part upon a comparison between the determined measure of complexity and a predetermined value.

The imaging the imaging data can be two dimensional x-ray imaging data, CT imaging data, MR imaging data, ultrasound imaging data, or any other imaging modality from which it is possible to assess the complexity of the body lumens through which the procedure will be conducted.

Among the various parameters that can be determined based upon the complexity score are one or more of the method of performing the procedure, (e.g., whether to perform the procedure manually or with automated assistance, such as with an remote medical navigation system), the identity of at least one device used in performing the procedure, the identity of at least one person to perform the procedure, or the selection between two or more alternative paths.

The complexity score can be used to estimate the duration of the procedure. This estimate can be based in part on the identity of the person performing the procedure, and this estimate can be used to select the person to perform the procedure. The estimate can be based in part on the path for the procedure, and this estimate can be used to select the path for the procedure. The estimate can also be used to generating a recommendation about the facility to perform the procedure and the time to start the procedure.

The parameter can also be which of a plurality of alternate paths through the vasculature to use in performing the procedure. The path can be chosen by estimating the duration of the procedure using each of the paths, and selecting the path with the shortest estimated procedure duration. The estimated duration can be made taking into account the identity of at least one person performing the procedure.

The parameter can also be the facility in which to perform the procedure and the time to start the procedure. The recommendation can be made by estimating the duration of the procedure based upon the determined measure of complexity and upon procedure duration for the individual performing the procedure correlated to the measure of complexity.

The parameter can also be the facility to perform the procedure. The recommendation can be made by estimating the duration of the procedure based upon the determined measure of complexity, and determining whether the facility is free for at least the estimated duration. Alternatively, the recommendation can be made by estimating the duration of the procedure based upon the determined measure of complexity and upon the identity of at least one person performing the procedure. Alternatively, the recommendation can be made by estimating the duration of the procedure based upon the determined measure of complexity and upon procedure duration data for the individual performing the procedure correlated to the measure of complexity.

The parameter can also be the time at which to perform the procedure. The recommendation can be made by estimating the duration of the procedure based upon the determined measure of complexity. Alternatively, the recommendation can be made by estimating the duration of the procedure based upon the determined measure of complexity and upon the identity of at least one person performing the procedure. Alternatively, the recommendation can be made by estimating the duration of the procedure based upon the determined measure of complexity and upon procedure data for the individual performing the procedure correlated to the measure of complexity.

The recommendation can encompass more than one parameter for the procedure. For example, the recommendation can include two parameters such as the facility to perform the procedure and the time to start the procedure. The recommendation can be made by estimating the duration of the procedure based upon the determined measure of complexity, and determining whether the facility is free for at least the estimated duration. Alternatively, the recommendation can be made by estimating the duration of the procedure based upon the determined measure of complexity and upon the identity of at least one person performing the procedure. Alternatively, the recommendation can be made by estimating the duration of the procedure based upon the determined measure of complexity and upon procedure duration for the individual performing the procedure correlated to the measure of complexity.

The recommendation could also encompass at least three parameters, for example the identity of person to conduct the procedure, the facility to perform the procedure, and the time to start the procedure.

The complexity score can be determined in a number of different ways, depending upon the features that make navigation difficult. In general, sharp bends, closely adjacent bends, and constrictions are significant obstacles to vasculature. Thus, the measure of the complexity of at least a portion of the vasculature is at least in part determined by whether any bend in the vasculature exceeds a predetermined angle. Alternatively or additionally, the measure of the complexity of at least a portion of the vasculature is at least in part determined by the number of bends in the vasculature that exceed a predetermined angle. Alternatively or additionally, the measure of the complexity of at least a portion of the vasculature is at least in part determined by the number of bends that exceed each of at least two predetermined angles. Alternatively or additionally, the measure of the complexity of at least a portion of the vasculature is at least in part determined by the minimum distance between bends in the vasculature that exceed a predetermined angle. Alternatively or additionally, the measure of the complexity of at least a portion of the vasculature is at least in part determined by the minimum vessel size.

Thus, one embodiment of the methods of this invention is a method of screening subjects for medical procedures involving the remote navigation of a medical device through the vasculature in an operating region in a subject. In accordance with this embodiment, the method comprises imaging the operating region including the vasculature to create image data of the operating region; processing the image data of the operating region to determine a measure of the complexity of at least a portion of the vasculature in the operating region; and comparing a the determined measure of complexity with a predetermined value to determine a parameter of the procedure.

Another embodiment of the methods of this invention is a method of scheduling medical procedures involving the remote navigation of a medical device through the vasculature in an operating region in a subject. In accordance with this embodiment the method comprises imaging the operating region including the vasculature to create image data of the operating region; processing the image data of the operating region to determine a measure of the complexity of at least a portion of the vasculature in the operating region; estimating the duration of the procedure based upon the determined measure of complexity; and scheduling the procedure based in part upon the estimated duration of the procedure.

Still another embodiment of the methods of this invention is a method of selecting a physician to perform a medical procedure involving the remote navigation of a medical device through the vasculature in an operating region in a subject. In accordance with this embodiment the method comprises imaging the operating region including the vasculature to create image data of the operating region; processing the image data of the operating region to determine a measure of the complexity of at least a portion of the vasculature in the operating region; comparing the determined measure of complexity with a proficiency score for each of a plurality of physicians; and selecting a physician whose proficiency score exceeds the determine measured of complexity.

Still another embodiment of the methods of this invention is a method of selecting a medical device for use in performing a medical procedure involving the remote navigation of a medical device through the vasculature in an operating region in a subject. In accordance with this embodiment the method comprises imaging the operating region including the vasculature to create image data of the operating region; processing the image data of the operating region to determine a measure of the complexity of at least a portion of the vasculature in the operating region; comparing the determined measure of complexity with a navigability score for each of a plurality of medical devices; and selecting a device whose navigability score exceeds the determined measured of complexity.

Still another embodiment of the methods of this invention is a method of selecting a procedure room for a medical procedure involving the remote navigation of a medical device through the vasculature in an operating region in a subject. In accordance with this embodiment, the method comprises imaging the operating region including the vasculature to create image data of the operating region; processing the image data of the operating region to determine a measure of the complexity of at least a portion of the vasculature in the operating region; using the determined measure of complexity to estimate the duration of the procedure; and selecting a procedure room that is available for the estimated duration.

Still another embodiment of the methods of this invention is a method of determining whether to perform a medical procedure involving the remote navigation of a medical device through the vasculature in an operating region in a subject manually or with automated assistance. In accordance with this embodiment, the method comprises imaging the operating region including the vasculature to create image data of the operating region; processing the image data of the operating region to determine a measure of the complexity of at least a portion of the vasculature in the operating region; comparing a the determined measure of complexity with a predetermined value; using automated assistance if the measure of complexity exceed the predetermined value.

In another aspect, embodiments of the methods of this invention provide a method of selecting one of a plurality of alternative navigation paths for performing a medical procedure involving the remote navigation of a medical device through the vasculature in an operating region in a subject. In accordance with this embodiment, the method comprises processing the image data of the operating region to determine a measure of the complexity of each of at least two paths through the vasculature in the operating region; comparing the measure of complexity for each of the at least two paths; using the path with the lowest measure of complexity. In another aspect, embodiments of the methods of this invention provide a method of estimating the duration of a medical procedure involving the remote navigation of a medical device through the vasculature in an operating region in a subject. In accordance with this embodiment, the method comprises imaging the operating region including the vasculature to create image data of the operating region; processing the image data of the operating region to determine a measure of the complexity of the path; and using the determined measure of complexity to estimate the duration of the procedure.

In another aspect, embodiments of the methods of this invention provide a method of screening subjects for medical procedures involving the remote navigation of a medical device through the vasculature in an operating region. In accordance with this embodiment, the method comprises processing the image data of the operating region to determine a measure of the complexity of at least a portion of the vasculature in the operating region; and comparing the determined measure of complexity with a predetermined value to generate a recommendation between at least two alternatives relating to a parameter for conducting the medical procedure.

In another aspect, embodiments of this invention provide a method of predicting the outcome of a medical procedure involving the remote navigation of a medical device through the vasculature in an operating region. In accordance with this embodiment, the method comprises processing the image data of the operating region to determine a measure of the complexity of at least a portion of the vasculature in the operating region; and generating an indicator of whether the navigation will be successfully completed based at least in part on the determined measure of complexity and physician specific success data correlated to the measure of complexity.

In another aspect, embodiments of this invention provide a method of selecting a physician for performing a medical procedure.

What is claimed is:

1. A method of screening subjects for medical procedures involving the remote navigation of a medical device through the vasculature in an operating region, the method comprising: using a processor to perform the following steps:
    processing the image data of the operating region;
    obtaining from the image data at least one measured value pertaining to the vasculature that is selected from the group consisting of the number of bends, the minimum distance between bends, the greatest bend angle, and the minimum size of the vasculature lumen, to determine a measure of the complexity of at least a portion of the vasculature in the operating region based on at least one measured value;
    generating a recommendation about at least one parameter of a subsequent procedure to be performed based at least in part upon a comparison between the determined measure of complexity and a predetermined value.

2. The method according to claim 1 wherein the image data is obtained from the subjects existing medical records.

3. The method according to claim 1 wherein the image date is obtained immediately prior to the medical procedure.

4. The method according to claim 1 wherein the imaging data is two dimensional x-ray imaging data.

5. The method according to claim 1 wherein the imaging data is CT imaging data.

6. The method according to claim 1 wherein the imaging data is MR imaging data.

7. The method according to claim 1 wherein the imaging data is ultrasound imaging data.

8. The method according to claim 1 wherein the parameter is the method of performing the procedure.

9. The method according to claim 8 wherein the parameter is whether to perform the procedure manually or with automated assistance.

10. The method according to claim 8 wherein the parameter is whether to perform the procedure manually or with a remote medical navigation system.

11. The method according to claim 8 wherein the parameter is whether to perform the procedure manually or with a remote magnetic navigation system.

12. The method according to claim 1 wherein the parameter is the identity of at least one device used in performing the procedure.

13. The method according to claim 1 wherein the parameter is the identity of at least one person to perform the procedure.

14. The method according to claim 13 wherein the step of generating a recommendation about the identity of at least one person based at least in part upon a comparison between the determined measure of complexity and a predetermined value includes estimating the duration of the procedure for each of the persons based upon the determined measure of complexity, and selecting the person based on the estimated duration.

15. The method according to claim 13 wherein the step of generating a recommendation about the path based at least in part upon a comparison between the determined measure of complexity and a predetermined value includes estimating the duration of the procedure based upon the determined measure of complexity and upon procedure duration data for each of a plurality of persons correlated to the determined measure of complexity, and selecting the person based on the estimated duration of the procedure.

16. The method according to claim 13 wherein the step of generating a recommendation about the facility to perform the procedure and the time to start the procedure based at least in part upon a comparison between the determined measure of complexity and a predetermined value includes estimating the success of the duration of the procedure based upon the determined measure of complexity and upon procedure duration for the individual performing the procedure correlated to the measure of complexity.

17. The method according to claim 1 wherein the parameter is which of a plurality of alternate paths through the vasculature to use in performing the procedure.

18. The method according to claim 17 wherein the step of generating a recommendation about the path based at least in part upon a comparison between the determined measure of complexity and a predetermined value includes estimating the duration of the procedure based upon the determined measure of complexity for each of the plurality of paths, and selecting the path with the shortest estimated procedure duration.

19. The method according to claim 17 wherein the step of generating a recommendation about the path based at least in part upon a comparison between the determined measure of complexity and a predetermined value includes estimating the duration of the procedure based upon the determined measure of complexity and upon the identity of at least one person performing the procedure, and selecting the path with the shortest estimated procedure duration.

20. The method according to claim 17 wherein the step of generating a recommendation about the facility to perform the procedure and the time to start the procedure based at least in part upon a comparison between the determined measure of complexity and a predetermined value includes estimating the duration of the procedure based upon the determined measure of complexity and upon procedure duration for the individual performing the procedure correlated to the measure of complexity.

21. The method according to claim 1 wherein the parameter is the facility to perform the procedure.

22. The method according to claim 21 wherein the step of generating a recommendation about the facility to perform the procedure based at least in part upon a comparison between the determined measure of complexity and a predetermined value includes estimating the duration of the procedure based upon the determined measure of complexity, and determining whether the facility is free for at least the estimated duration.

23. The method according to claim 21 wherein the step of generating a recommendation about the facility to perform the procedure based at least in part upon a comparison between the determined measure of complexity and a predetermined value includes estimating the duration of the procedure based upon the determined measure of complexity and upon the identity of at least one person performing the procedure.

24. The method according to claim 21 wherein the step of generating a recommendation about the facility to perform the procedure based at least in part upon a comparison between the determined measure of complexity and a predetermined value includes estimating the duration of the procedure based upon the determined measure of complexity and upon procedure duration data for the individual performing the procedure correlated to the measure of complexity.

25. The method according to claim 1 wherein the parameter is the time at which to perform the procedure.

26. The method according to claim 25 wherein the step of generating a recommendation about at least one parameter of the procedure based at least in part upon a comparison between the determined measure of complexity and a predetermined value includes estimating the duration of the procedure based upon the determined measure of complexity.

27. The method according to claim 25 wherein the step of generating a recommendation about at least one parameter of the procedure based at least in part upon a comparison between the determined measure of complexity and a predetermined value includes estimating the duration of the procedure based upon the determined measure of complexity and upon the identity of at least one person performing the procedure.

28. The method according to claim 25 wherein the step of generating a recommendation about at least one parameter of the procedure based at least in part upon a comparison between the determined measure of complexity and a predetermined value includes estimating the duration of the procedure based upon the determined measure of complexity and upon proceduration data for the individual performing the procedure correlated to the measure of complexity.

29. The method according to claim 1 wherein there are at least two parameters, including the facility to perform the procedure and the time to start the procedure.

30. The method according to claim 29 wherein the step of generating a recommendation about the facility to perform the procedure and the time to start the procedure based at least in part upon a comparison between the determined measure of complexity and a predetermined value includes estimating the duration of the procedure based upon the determined measure of complexity, and determining whether the facility is free for at least the estimated duration.

31. The method according to claim 29 wherein the step of generating a recommendation about the facility to perform the procedure and the time to start the procedure based at least in part upon a comparison between the determined measure of complexity and a predetermined value includes estimating the duration of the procedure based upon the determined measure of complexity and upon the identity of at least one person performing the procedure.

32. The method according to claim 29 wherein the step of generating a recommendation about the facility to perform the procedure and the time to start the procedure based at least in part upon a comparison between the determined measure of complexity and a predetermined value includes estimating the duration of the procedure based upon the determined measure of complexity and upon procedure duration for the individual performing the procedure correlated to the measure of complexity.

33. The method according to claim 1 wherein there are at least three parameters, including the identity of person to conduct the procedure, the facility to perform the procedure, and the time to start the procedure.

34. The method according to claim 1 wherein the measure of the complexity of at least a portion of the vasculature is at least in part determined by whether any bend in the vasculature exceeds a predetermined angle.

35. The method according to claim 1 wherein the measure of the complexity of at least a portion of the vasculature is at least in part determined by the number of bends in the vasculature that exceed a predetermined angle.

36. The method according to claim 1 wherein the measure of the complexity of at least a portion of the vasculature is at least in part determined by the number of bends that exceed each of at least two predetermined angles.

37. The method according to claim 1 wherein the measure of the complexity of at least a portion of the vasculature is at least in part determined by the minimum distance between bends in the vasculature that exceed a predetermined angle.

38. The method according to claim 1 wherein the measure of the complexity of at least a portion of the vasculature is at least in part determined by the minimum vessel size.

39. A method of screening subjects for medical procedures involving the remote navigation of a medical device through the vasculature in an operating region in a subject, the method comprising: using a processor to perform the following steps:
    imaging the operating region including the vasculature to create image data of the operating region;
    obtaining from the image data at least one measured value pertaining to the vasculature that is selected from the group consisting of the number of bends, the minimum distance between bends, the greatest bend angle, and the minimum size of the vasculature lumen;
    processing the image data of the operating region to determine a measure of the complexity of at least a portion of the vasculature in the operating region based on at least one measured value;
    comparing the determined measure of complexity with a predetermined value to determine a parameter of a subsequent procedure to be performed based at least in part upon the comparison between the determined measure of complexity and the predetermined value.

40. A method of scheduling medical procedures involving the remote navigation of a medical device through the vasculature in an operating region in a subject, the method comprising: using a processor to perform the following steps:
    imaging the operating region including the vasculature to create image data of the operating region;
    obtaining from the image data at least one measured value pertaining to the vasculature that is selected from the group consisting of the number of bends, the minimum distance between bends, the greatest bend angle, and the minimum size of the vasculature lumen;
    processing the image data of the operating region to determine a measure of the complexity of at least a portion of the vasculature in the operating region based on at least one measured value;
    estimating the duration of the procedure based upon the determined measure of complexity; and
    scheduling a subsequent procedure to be performed based in part upon the estimated duration of the procedure.

41. A method of selecting a physician to perform a medical procedure involving the remote navigation of a medical device through the vasculature in an operating region in a subject, the method comprising: using a processor to perform the following steps:
    imaging the operating region including the vasculature to create image data of the operating region;
    obtaining from the image data at least one measured value pertaining to the vasculature that is selected from the group consisting of the number of bends, the minimum distance between bends, the greatest bend angle, and the minimum size of the vasculature lumen;
    processing the image data of the operating region to determine a measure of the complexity of at least a portion of the vasculature in the operating region based on at least one measured value;
    comparing the determined measure of complexity with a proficiency score for each of a plurality of physicians; and
    selecting, for a subsequent procedure to be performed, a physician whose proficiency score exceeds the determined measured of complexity.

42. A method of selecting a medical device for use in performing a medical procedure involving the remote navigation of a medical device through the vasculature in an operating region in a subject, the method comprising: using a processor to perform the following steps:
    imaging the operating region including the vasculature to create image data of the operating region;
    obtaining from the image data at least one measured value pertaining to the vasculature that is selected from the group consisting of the number of bends, the minimum distance between bends, the greatest bend angle, and the minimum size of the vasculature lumen;
    processing the image data of the operating region to determine a measure of the complexity of at least a portion of the vasculature in the operating region based on at least one measured value;
    comparing the determined measure of complexity with a navigability score for each of a plurality of medical devices; and
    selecting, for a subsequent procedure to be performed, a device whose navigability score exceeds the determined measured of complexity.

43. A method of selecting a procedure room for a medical procedure involving the remote navigation of a medical device through the vasculature in an operating region in a subject, the method comprising: using a processor to perform the following steps:
    imaging the operating region including the vasculature to create image data of the operating region;
    obtaining from the image data at least one measured value pertaining to the vasculature that is selected from the group consisting of the number of bends, the minimum distance between bends, the greatest bend angle, and the minimum size of the vasculature lumen;

processing the image data of the operating region to determine a measure of the complexity of at least a portion of the vasculature in the operating region based on at least one measured value;

using the determined measure of complexity to estimate the duration of a subsequent procedure to be performed;

selecting, for the subsequent procedure to be performed, a procedure room that is available for the estimated duration.

44. A method of determining whether to perform a medical procedure involving the remote navigation of a medical device through the vasculature in an operating region in a subject manually or with automated assistance, the method comprising: using a processor to perform the following steps:

imaging the operating region including the vasculature to create image data of the operating region;

obtaining from the image data at least one measured value pertaining to the vasculature that is selected from the group consisting of the number of bends, the minimum distance between bends, the greatest bend angle, and the minimum size of the vasculature lumen;

processing the image data of the operating region to determine a measure of the complexity of at least a portion of the vasculature in the operating region based on at least one measured value;

comparing the determined measure of complexity with a predetermined value;

using automated assistance, for a subsequent procedure to be performed, if the measure of complexity exceed the predetermined value.

45. A method of selecting one of a plurality of alternative navigation paths for performing a medical procedure involving the remote navigation of a medical device through the vasculature in an operating region, the method comprising: using a processor to perform the following steps:

imaging the operating region including the vasculature to create image data of the operating region;

obtaining from the image data at least one measured value pertaining to the vasculature that is selected from the group consisting of the number of bends, the minimum distance between bends, the greatest bend angle, and the minimum size of the vasculature lumen;

processing the image data of the operating region to determine a measure of the complexity of each of at least two paths through the vasculature in the operating region based on at least one measured value;

comparing the measure of complexity for each of the at least two paths;

using the path with the lowest measure of complexity for a subsequent procedure to be performed.

46. A method of estimating the duration of a medical procedure involving the remote navigation of a medical device through the vasculature in an operating region in a subject, the method comprising: using a processor to perform the following steps:

imaging the operating region including the vasculature to create image data of the operating region;

obtaining from the image data at least one measured value pertaining to the vasculature that is selected from the group consisting of the number of bends, the minimum distance between bends, the greatest bend angle, and the minimum size of the vasculature lumen;

processing the image data of the operating region to determine a measure of the complexity of the path based on at least one measured value; and using the determined measure of complexity to estimate the duration of a subsequent procedure to be performed.

47. A method of screening subjects for medical procedures involving the remote navigation of a medical device through the vasculature in an operating region, the method comprising: using a processor to perform the following steps:

obtaining from the image data at least one measured value pertaining to the vasculature that is selected from the group consisting of the number of bends, the minimum distance between bends, the greatest bend angle, and the minimum size of the vasculature lumen;

processing the image data of the operating region to determine a measure of the complexity of at least a portion of the vasculature in the operating region based on at least one measured value;

comparing the determined measure of complexity with a predetermined value to generate a recommendation between at least two alternatives relating to a parameter for conducting a subsequent medical procedure to be performed.

48. A method of predicting the outcome of a medical procedure involving the remote navigation of a medical device through the vasculature in an operating region, the method comprising: using a processor to perform the following steps:

obtaining from the image data at least one measured value pertaining to the vasculature that is selected from the group consisting of the number of bends, the minimum distance between bends, the greatest bend angle, and the minimum size of the vasculature lumen;

processing the image data of the operating region to determine a measure of the complexity of at least a portion of the vasculature in the operating region based on at least one measured value;

generating an indicator of whether the navigation will be successfully completed in a subsequent procedure to be performed, based at least in part on the determined measure of complexity and physician specific success data correlated to the measure of complexity.

* * * * *